United States Patent [19]

Babine et al.

[11] Patent Number: 4,866,169

[45] Date of Patent: Sep. 12, 1989

[54] 3-SUBSTITUTED-8-OXO-7-SUBSTITUTED-THIOXOMETHYLAMINO-5-THIA-1-AZABICYCLO-(4.2.0)OCT-2-ENE-2-CARBOXYLIC ACID, DIPHENYLMETHYL ESTERS

[75] Inventors: Robert Babine, Pomona; William V. Curran, Pearl River; Ving J. Lee, Monsey, all of N.Y.

[73] Assignee: American Cyanamid Company, Stamford, Conn.

[21] Appl. No.: 920,398

[22] Filed: Oct. 20, 1986

[51] Int. Cl.[4] .................. C07D 501/36; A61K 31/545
[52] U.S. Cl. .................................... 540/226; 540/230; 540/310; 540/314

[58] Field of Search ............... 540/230, 222, 314, 225, 540/226, 227, 310, 215

[56] References Cited

U.S. PATENT DOCUMENTS 3,926,974  12/1975  Nudelman et al. ................. 540/215

OTHER PUBLICATIONS

Chemical Abstracts vol. 99 122120(d) (1983).
Chemical Abstracts vol. 103 123223(c) 1985.

*Primary Examiner*—Nicholas S. Rizzo
*Attorney, Agent, or Firm*—Robert P. Raymond

[57] ABSTRACT

Diphenylmethyl esters of cephalosporins, and processes for synthesizing such, are described and disclosed.

4 Claims, No Drawings

3-SUBSTITUTED-8-OXO-7-SUBSTITUTED-THIOXOMETHYLAMINO-5-THIA-1-AZABICYCLO-(4.2.0)OCT-2-ENE-2-CARBOXYLIC ACID, DIPHENYLMETHYL ESTERS

SUMMARY OF THE INVENTION

This invention is concerned with compounds of Formula I:

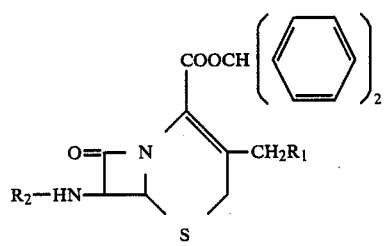

FORMULA I wherein $R_1$ is hydrogen, alkyl($C_1$-$C_3$), vinyl, acetyloxy or

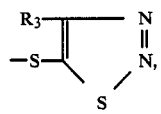

where
$R_3$ is hydrogen or alkyl($C_1$-$C_6$); and
$R_2$ is

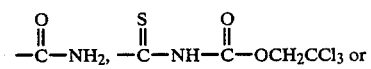

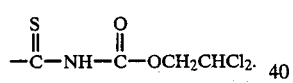

The invention is further concerned with compounds of Formula II:

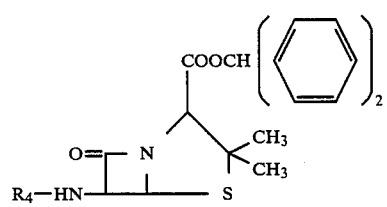

FORMULA II where $R_4$ is

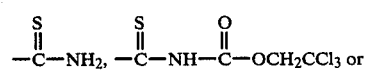

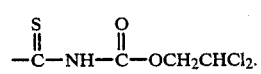

This invention is further concerned with processes for the production of these compounds as well as their use as intermediates in the preparation of biologically active 7-aminocephalosporanic acids which are the subject of copending and co-owned application for U.S. Pat. No. 420,397 filed Oct. 20, 1986, filed concurrently herewith, the disclosure and contents thereof are hereby incorporated by reference.

DESCRIPTION OF THE INVENTION

The compounds of this invention may be prepared according to the following reaction schemes.

Scheme A 7-aminocephalosporanic acid, diphenylmethyl ester

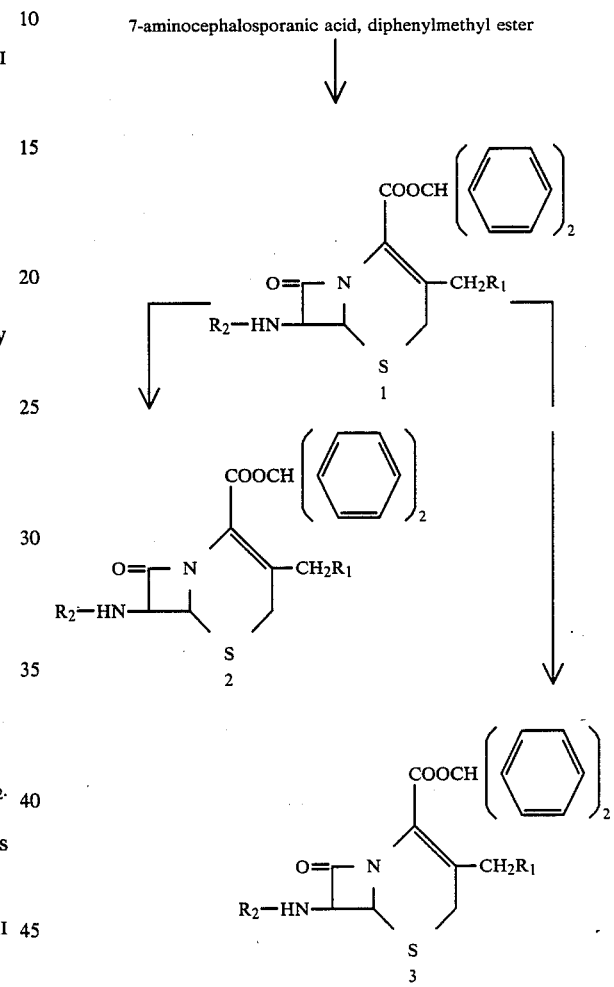

According to Scheme A, a 7-aminocephalosporanic acid, diphenylmethyl ester where $R_1$ is as described above is reacted with 2,2,2-trichloroethoxycarbonylisothiocyanate in a solvent such as dichloromethane giving a 3-substituted-8-oxo-7-[[thioxo[[(2,2,2-trichloroethoxy)carbonyl]amino]methyl]amino]-5-thia-1-azabicyclo[4.2.0]oct-2-ene-2-carboxylic acid, diphenylmethyl ester, 1, where $R_1$ is as described above and $R_2$ is

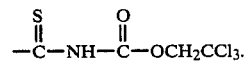

Compound 1M is then reacted with zinc dust, glacial acetic acid and 1M potassium dihydrogen phosphate in tetrahydrofuran, giving compound 2, a 3-substituted-7-[[[[(2,2-dichloroethoxy)carbonyl]amino]thioxomethyl]amino]-8-oxo-5-thia-1-azabicyclo[4.2.0]oct-2-ene-2-carboxylic acid, diphenylmethyl ester and compound 3, a 3-substituted-7-[(aminothioxomethyl)amino]-8-oxo-5- thia-1-azabicyclo[4.2.0]oct-2-ene-2-carboxylic acid, diphenylmethyl ester where $R_1$ is as described above and $R_2$ is

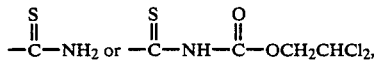

which compounds are separated and purified by chromatography.

Scheme B

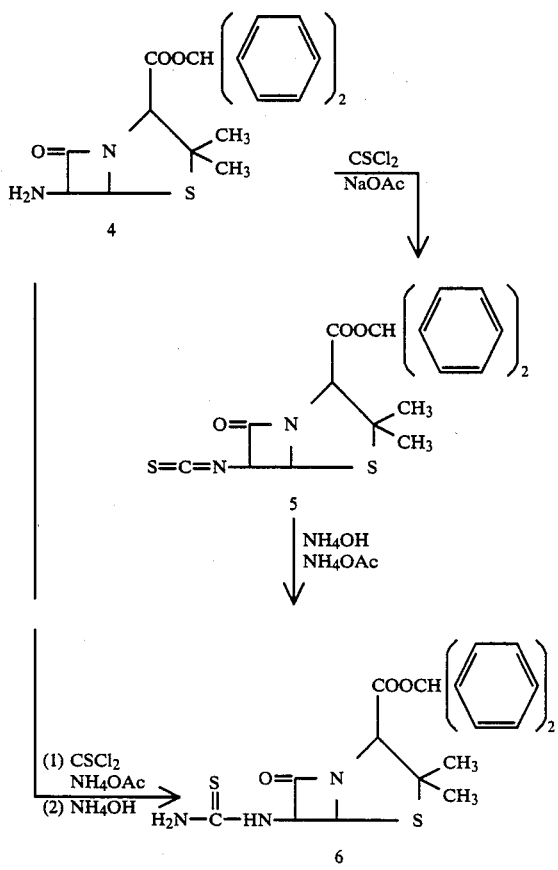

According to Scheme B, 6-aminopenicillanic acid, diphenylmethyl ester 4 is reacted with thiophosgene and sodium acetate in ethyl acetate giving the isothiocyanate derivative 5, which is then reacted with ammonium acetate in ethyl acetate and water, giving the thiourea derivative 6.

Alternatively 4 may be converted directly to 6 without isolation of 5 by reacting 4 as described above and then adding ammonium hydroxide incrementally.

The reaction described in Scheme B may also be used to convert 7-aminocephalosporanic acid, diphenylmethyl esters 1 (Scheme A) to the corresponding thiourea derivatives 3 (Scheme A).

The compounds of this invention are then converted to compounds of the formula:

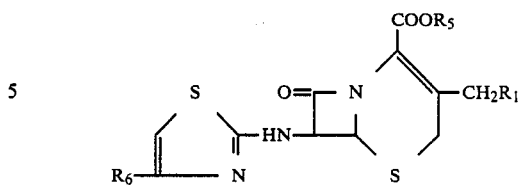

where $R_1$ is as described above, $R_5$ is hydrogen, sodium or potassium and $R_6$ is phenyl, COOH, COOalkyl($C_1$–$C_3$), alkyl($C_1$–$C_3$) or $COOCH_2CCl_3$, which are active antibacterial agents.

This invention is further described by the following non-limiting examples.

EXAMPLE 1

(6-R-trans)-3-[(Acetyloxy)methyl]-8-oxo-7-[[thioxo[[(2,2,2-trichloroethoxy)carbonyl]amino]methyl]amino]-5-thia-1-azabicyclo[4.2.0]oct-2-ene-2-carboxylic acid, diphenylmethyl ester A mixture 4.03 g of carbon(isothiocyanatidic) acid, 2,2,2-trichloroethyl ester, 7.49 g of (6R-trans)-3-[(acetyloxy)methyl-7-amino-8-oxo-5-thia-1-azabicyclo[4.2.0]oct-2-ene-2-carboxylic acid, diphenylmethyl ester and 125 ml of dichloromethane was stirred for 30 minutes, then filtered through hydrous magnesium silicate and evaporated giving 11.47 g of the desired compound $[\alpha]_D^{26} = +29° \pm 2°$ (c 0.51% $CHCl_3$).

EXAMPLE 2

(6R-trans)-3-[(Acetyloxy)methyl]-7-[(aminothioxomethyl)amino]-8-oxo-5-thia-1-azabicyclo[4.2.0]oct-2-ene-2-carboxylic acid, diphenylmethyl ester and (6R-trans)-3-[(acetyloxy)methyl]-7-[[[[(2,2-dichloroethoxy)carbonyl]amino]thioxomethyl]amino]-8-oxo-5-thia-1-azabicyclo[4.2.0]oct-2-ene-2-carboxylic acid, diphenylmethyl ester A mixture of 1.16 g of (6R-trans)-3-[(acetyloxy)methyl]-8-oxo-7-[[thioxo[[(2,2,2-trichloroethoxy)carbonyl]amino]methyl]amino]-5-thia-1-azabicyclo[4.2.0]oct-2-ene-2-carboxylic acid, diphenylmethyl ester, 660 mg of zinc dust, 0.25 ml of glacial acetic acid, 2 ml of 1M aqueous potassium dihydrogen phosphate and 10 ml of tetrahydrofuran was stirred for 1 hour and then filtered. The filtrate was subjected to flash chromatography, eluting with ethyl acetate:petroleum ether in a 1:1 to 1:2 gradient, giving 340 mg of (6R-trans)-3-[(acetyloxy)methyl]-7-[(aminothioxomethyl)amino]-8-oxo-5-thia-1-azabicyclo[4.2.0]oct-2-ene-2-carboxylic acid, diphenylmethyl ester and 30 mg of (6R-trans)-3-[(acetyloxy)methyl]-7-[[[[(2,2-dichloroethoxy)carbonyl]amino]thioxomethyl]amino]-8-oxo-5-thia-1-azabicyclo[4.2.0]oct-2-ene-2-carboxylic acid, diphenylmethyl ester.

EXAMPLE 3

[2S-(2α,5α,6β)]-3,3-Dimethyl-7-oxo-6-[[thioxo[[(2,2,2-trichloroethoxy)carbonyl]amino]methyl]amino]-4-thia-1-azabicyclo[3.2.0]heptane-2-carboxylic acid, diphenylmethyl ester 5.0 ml portion of trichloroethoxy chloroformate was added dropwise to a warm (50° C.) solution of potassium thiocyanate in 100 ml acetonitrile. This solution was stirred at 50° C. for 20 minutes, then allowed to cool to room temperature and chilled in an ice bath. The resulting solution was filtered and concentrated in vacuo. Vacuum distillation of the residue at 70° C., 1 mm Hg, gave 7.60 g of 2,2,2-trichloroethoxycarbonylthiocyanate.

A 14.04 g portion of 6-aminopencillanic acid benzhydryl ester pTSOH salt was partitioned between 150 ml of dichloromethane and saturated aqueous sodium bicarbonate. The dichloromethane layer was separated and dried over sodium sulfate. To this solution was added 5.63 g of 2,2,2-trichloroethoxycarbonylthiocyanate. This mixture was stirred for 1 hour, filtered through hydrous magnesium silicate and concentrated, giving 13.3 g of the desired product as a white foam.

EXAMPLE 4

3,3-Dimethyl-6-isothiocyanato-7-oxo-4-thia-1-azabicyclo[3.2.0]heptane-2-carboxylic acid, diphenylmethyl ester A 555 mg portion of 6-amino-3,3-dimethyl-7-oxo-4-thia-1-azabicyclo[3.2.0]heptane-2-carboxylic acid, diphenylmethyl ester was dissolved in 20 ml of ethyl acetate. A 400 mg portion of sodium acetate was dissolved in 10 ml of water and added to the above solution. A 0.09 ml portion of thiosphosgene was added, the mixture was stirred 15 minutes and the layers separated. The organic layer was washed with brine, dried and evaporated, giving 447 mg of the desired compound.

EXAMPLE 5

6-[(Aminothioxomethyl)-3,3-dimethyl-7-oxo-4-thia-1-azabicyclo[3.2.0]heptane-2-carboxylic acid, diphenylmethyl ester A 447 mg portion of 3,3-dimethyl-6-isothiocyanato-7-oxo-4-thia-1-azabicyclo[3.2.0]heptane-2-carboxylic acid, diphenylmethyl ester was dissolved in 15 ml of ethyl acetate. A solution of 1 g of ammonium acetate in 10 ml of water was added. Six drops of concentrated ammonium hydroxide were added with stirring. Stirring was continued for 1 hour, then the layers were separated. The organic layer was washed twice with brine, dried and evaporated to 5 ml. This was diluted to 100 ml with hexane and chilled. The solid was collected, giving 261 mg of the desired compound.

EXAMPLE 6

6-[(Aminothioxomethyl)amino]-3,3-dimethyl-7-oxo-4-thia-1-azabicyclo[3.2.0]heptane-2-carboxylic acid, diphenylmethyl ester A 0.9 ml portion of thiophosgene was added to a stirred mixture of 5.55 g of 6-amino-3,3-dimethyl-7-oxo-4-thia-1-azabicyclo[3.2.0]heptane-2-carboxylic acid, diphenylmethyl ester in 100 ml of ethyl acetate and 5.0 g of ammonium acetate in 50 ml of water. After stirring for 10-15 minutes concentrated ammonium hydroxide was added in increments over 5 hours. The layers were separated and the organic layer washed twice with brine, dried, evaporated to about 20 ml and chilled. The solid was collected, giving 2.385 g of the desired compound.

EXAMPLE 7

3-[(Acetyloxy)methyl]-7-isothiocyanato-8-oxo-5-thia-1-azabicyclo[4.2.0]oct-2-ene-2-carboxylic acid, diphenylmethyl ester The procedure of Example 4 was followed using 439 mg of 3-[(acetyloxy)methyl]-7-amino-8-oxo-5-thia-1-azabicyclo[4.2.0]oct-2-ene-2-carboxylic acid, diphenylmethyl ester and 240 mg of sodium acetate, giving 535 mg of the desired compound as a yellow oil.

EXAMPLE 8

(6R-cis)-3-[(Acetyloxy)methyl]-7-[(aminothioxomethyl)amino]-8-oxo-5-thia-1-azabicyclo[4.2.0]oct-2-ene-2-carboxylic acid, diphenylmethyl ester The procedure of Example 6 was followed using 4.39 g of 3-[(acetyloxy)methyl]-7-amino-8-oxo-5-thia-1-azabicyclo[4.2.0]oct-2-ene-2-carboxylic acid, diphenylmethyl ester. The resulting oil was dissolved in 25 ml of ethyl acetate, hexane was added with warming to enhance solution, then the mixture was allowed to stand for several hours and chilled. The resulting solid was removed by filtration and the filtrate evaporated to a glass. This glass was dissolved in a small amount of ethyl acetate, silica gel was added, the mixture evaporated to dryness and added to the top of a 150 g silica gel column. The column was flash chromatographed eluting as follows:

Fractions 1 to 8—8×80 ml of ethyl acetate:hexane (30:70)

Fractions 9 to 20—12×80 ml of ethylacetate:hexane (40:60)

Fractions 21 to 24—4×100 ml of ethylacetate:hexane (50:50)

Fractions 25 to 34—10×100 ml of ethyl acetate:hexane (30:20)

Fraction 31 was evaporated and crystallized from a small amount of ethyl acetate:hexane giving 44 mg of the desired compound as light yellow crystals.

What is claimed is:

1. A compound selected from those of the formula:

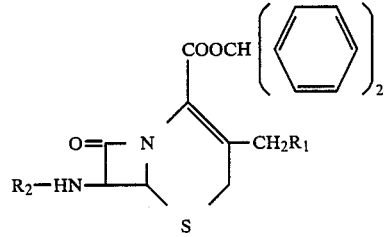

wherein $R_1$ is hydrogen, alkyl($C_1$–$C_3$), vinyl, acetyloxy or

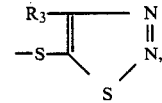

where $R_3$ is hydrogen or alkyl($C_1$–$C_6$); and $R_2$ is

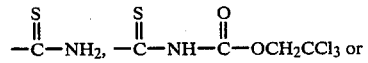 or

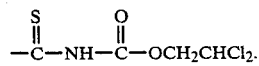

2. The compound according to claim 1, (6R-trans)-3-[(acetoxy)methyl]-8-oxo-7-[[thioxo[[2,2,2-trichloroethoxy)carbonyl]amino]methyl]amino]-5-thia-1-azabicyclo[4.2.0]oct-2-ene-2-carboxylic acid, diphenylmethyl ester.

3. The compound according to claim 1, (6R-trans)-3-[(acetyloxy)methyl]-7-[(aminothioxomethyl)amino]-8-oxo-5-thia-1-azabicyclo[4.2.0]oct-2-ene-2-carboxylic acid, diphenylmethyl ester.

4. The compound according to claim 1, (6R-trans)-3-[(acetyloxy)methyl]-7-[[[[(2,2-dichloroethoxy)carbonyl]amino]thioxomethyl]amino]-8-oxo-5-thia-1-azabicyclo[4.2.0]oct-2-ene-2-carboxylic acid, diphenylmethyl ester.

* * * * *